United States Patent [19]

Strack et al.

[11] Patent Number: 4,913,957
[45] Date of Patent: Apr. 3, 1990

[54] THERMAL RETAINING FABRIC LAMINATE

[75] Inventors: David C. Strack, Canton; La-Donna M. Brown, Dunwoody, both of Ga.

[73] Assignee: Kimberly-Clark Corporation, Neenah, Wis.

[21] Appl. No.: 197,377

[22] Filed: May 23, 1988

[51] Int. Cl.$^4$ ............................................. B32B 27/00
[52] U.S. Cl. ................................. 428/286; 128/399; 128/400; 128/403; 424/447; 424/449; 428/64; 428/289
[58] Field of Search .................. 428/64, 286, 287; 128/399, 400, 403; 424/447, 449

[56] References Cited

U.S. PATENT DOCUMENTS

| | | | |
|---|---|---|---|
| 2,562,121 | 7/1951 | Paux | 150/2.2 |
| 2,932,052 | 4/1960 | Morse | 15/209 |
| 3,657,760 | 4/1972 | Kudisch | 15/104.93 |
| 3,780,537 | 12/1973 | Spencer | 62/530 |
| 3,885,403 | 5/1975 | Spencer | 62/530 |
| 4,161,283 | 7/1979 | Hyman | 229/55 |
| 4,226,232 | 10/1980 | Spencer | 128/156 |
| 4,588,400 | 5/1986 | Ring et al. | 604/304 |
| 4,725,272 | 2/1988 | Gale | 424/448 |
| 4,725,439 | 2/1988 | Campbell | 424/449 |

Primary Examiner—Marion C. McCamish
Attorney, Agent, or Firm—William D. Herrick

[57] ABSTRACT

There is disclosed a thermal retaining fabric laminate which can be used as a hot or cold pack to impart heated or cooled treatment liquids to the skin of a user. The laminate consists in sequence of a skin contact layer for absorbing, holding, and delivering the treatment liquid, a nonporous or low porous first barrier layer, a reservoir layer for absorbing and holding heat retention liquid, and a nonporous second barrier layer. The laminate has an open edge. The barrier layers serve to inhibit the release of vapor while the fabric laminate is in contact with the skin of a user thereby decreasing heat loss resulting from evaporation and increasing the time that the fabric laminate retains its heat. In one embodiment, the first barrier layer between the skin contact layer and the reservoir layer is of low porosity which when the fabric laminate is heated rapidly allows for the escape of vapor so that the vapor pressure created in the reservoir layer will not delaminate the fabric laminate.

9 Claims, 1 Drawing Sheet

THERMAL RETAINING FABRIC LAMINATE

BACKGROUND OF THE INVENTION

This invention relates generally to a fabric laminate and more particularly concerns a fabric laminate which can be heated or cooled, can retain its heat or cold over a period of time, and as a consequence of that heat or cold can deliver a warm or cool treatment liquid to the skin of a user.

In a number of circumstances relating both to health care and beauty care, it is desirable to use a hot or cold pack to deliver a hot or cold treatment liquid to the skin of the user. The concept of applying a heated cosmetic lotion to the skin is old. Particularly, with regard to moisturizing lotions, it is known that warming the skin increases the flow of blood to the treated area and thereby, provides a more rapid diffusion of the lotion into the stratum corneum of the skin. Heated application of a moisturizing lotion also assures a more efficient spread of the lotion. With respect to a cosmetic cleanser, heated application increases the solubility of makeup on the user's skin in the cleanser. In the past, cosmetic lotions or cleansers were applied to a hot washcloth or towel and then applied to the skin. The heat retention for a wet textile towel is very short due to evaporation heat loss. Consequently, it was difficult to realize the full beneficial advantages that flowed from applying cosmetic lotions or cleansers in a heated form to the user's skin.

In addition to facial cosmetic treatments for beauty care, hot or cold packs and compresses are useful for medical treatment. For example, a hot compress can be impregnated with an analgesic formula and then applied directly to the skin to assist the absorption of the analgesic lotion into the skin which in combination with the increased blood flow resulting from the heating, speeds relief in sore joints and muscles. Hot packs can also be used as a poultice which may be applied to the user's chest to create a vapor atmosphere to relieve various nasal and respiratory ailments. In addition, cold packs in conjunction with an analgesic liquid may be used for the reduction of inflammation resulting from injury.

In order to achieve the benefits of treatment by a hot or cold pack, the pack must provide a skin contact surface which will readily absorb the treatment liquid and then transfer it on contact to the user's skin without leaching of other liquids or chemicals. The hot or cold pack must be able to retain its heat or cold over a period of time.

SUMMARY OF THE INVENTION

It is therefore an object of the present invention to provide a thermal retaining fabric laminate for use as a heat or cold pack for applying treatment lotions or liquids to the skin of a user and maintaining the lotion or liquids in a heated or cold condition for an appropriate period of time to allow the lotion or liquid to be absorbed by the skin.

It is likewise an object of the present invention to provide a hot or cold pack in which a small amount of lotion is impregnated in a skin contact surface layer of the fabric laminate in order to minimize the amount of lotion required in the hot or cold pack.

It is further an object of the present invention to provide a fabric laminate which has a heat retention liquid stored in a reservoir layer which is separated by a first low porous or nonporous barrier layer from the skin contact layer impregnated with a treatment lotion so that interreaction between the treatment lotion and the heat retention liquid is inhibited.

It is also an object of the present invention to provide a fabric laminate which can be heated by means of microwave energy without localized heating of the heat retention liquid disrupting the barrier layer between the skin contact layer and the reservoir layer.

The foregoing objectives are realized by a fabric laminate having in sequence a skin contact layer impregnated with a treatment lotion, a first nonporpous or low porous barrier layer, a reservoir layer impregnated with a heat retaining liquid, and a second nonporous barrier layer.

The skin contact layer consists of a thin soft absorbent layer for absorbing, holding, and delivering the treatment lotion. In the preferred embodiment, the skin contact layer is a melt-blown layer of thermoplastic fibers having a basis weight of between 0.5 and 2.0 ounces per yards square ($oz/yd^2$) and impregnated with the moisturizing liquid to at least 30% of its maximum liquid holding capacity. Such maximum capacity ranges from about 600% for bonded melt-blown layers to 1200% for unbonded melt-blown layers. In general, any thermal plastic material can be used for making such a melt-blown layer, but polypropylene is generally preferred.

The first barrier layer is a thermoplastic film which may be extruded onto the skin contact layer. Adhesion between the skin contact layer and first barrier layer may be enhanced by heat embossing a decorative pattern onto the two layers. Alternatively, the barrier layer may be a separate thermoplastic film which is adhesively attached to the skin contact layer. In one embodiment, the first barrier layer is a thermoplastic film with low porosity which allows vapor from the heat retaining liquid in the reservoir layer to escape during heating, particularly in connection with microwave heating where there may be localized hot spots, but which separates the treatment lotion in the skin contact layer from the heat retention liquid in the reservoir layer below. The low porosity of the first barrier layer may be achieved by extruding a very thin thermoplastic layer of 1.0 mil or less, generally about 0.5 mil, onto the melt-blown skin contact layer. The resulting thin thermoplastic film layer has inherent defects or pin holes therein which provide the appropriate degree of low porosity to vapors while at the same time separating the treatment lotion in the skin contact layer from the heat retention liquid in the reservoir layer. Where heating of the fabric laminate is carried out in a slow and uniform fashion, the first barrier layer may be increased in thickness up to about 3 mils at which point the barrier layer imparts undesirable stiffness to the fabric laminate. WIth a barrier layer of 1 to 3 mils in thickness, the barrier layer is impermeable to both vapor and moisture assuring a complete barrier between the treatment lotion in the skin contact layer and the heat retention liquid in the reservoir layer.

The reservoir layer is any appropriate absorbent which will absorb and hold a sufficient amount of heat retention liquid to retain heat or cold in the fabric laminate. Based on cost consideration, one preferably absorbent is co-form which is a blend of staple length and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Other suitable absorbents may include wood pulp fluff, cellulose wadding, open cell foam, or the like. Super-absorbents may be added to the foregoing absorbent media to increase capacity. The heat retention liquid may be water or a salt solution. surfactants to assist in speeding absorbency may be added to the heat retention liquid.

Other object and advantages of the invention will become apparent upon reading the following detailed description and upon reference to the drawings.

DETAILED DESCRIPTION OF THE INVENTION

While the invention will be described in connection with a preferred embodiment, it will be understood that we do not intend to limit the invention to that embodiment. On the contrary, we intend to cover all alternative, modifications, and equivalents as may be included within the spirit and scope of the invention as defined by the appended claims.

Figure 2:
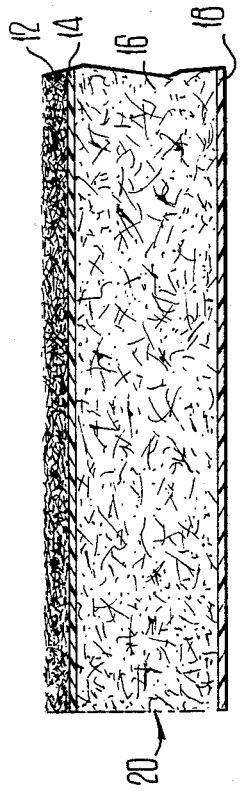
FIG. 2 is a cross-section view of the thermal retaining fabric laminate of the present invention.
Figure 1:
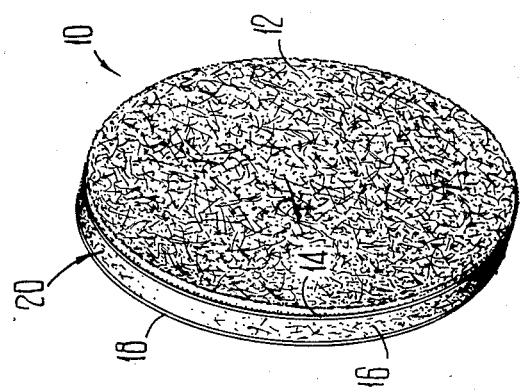
FIG. 1 is a perspective view of the thermal retaining fabric laminate of the present invention.

Turning to FIG. 1, there is shown a thermal retaining fabric laminate 10 which may be impregnated with a treatment lotion, heated, and used to apply the heated treatment lotion to the face of a user. The fabric laminate 10 as best shown in FIG. 2, comprises a skin contact layer 12 which is impregnated with the treatment lotion, a first nonporous or low porous barrier layer 14, a reservoir layer 16 which is impregnated with a heat retention liquid, and a second nonporous barrier layer 18. The fabric laminate 10 has an open edge 20.

The skin contact layer 12 consists of a thin soft absorbent layer capable of absorbing, holding, and delivering an effective amount of treatment liquid. The skin contact layer may be of any suitable fabric-like material including a carded web, a woven fabric, or a nonwoven fabric such as a spun-bonded web or a melt-blown web. A melt-blown web, because of its surface softness and absorbency, is preferred. The melt-blown layer 12 consists of intermingled discrete fibers which may be produced by conventional melt-blowing techniques which are well within the skill of those of ordinary skill in the art. Such skill is demonstrated by NRL Report 4364, "Manufactured of Super-Fine Organic Fibers", by V. A. Wendt, E. L. Boon, and C. D. Fluharty; NRL Report 5265, "An Improved Device for the Formation of Super-Fine Thermoplastic Fibers", by K. D. Lawrence, R. T. Lukas, and J. A. Young; and, U.S. Pat. No. 3,849,241, issued Nov. 19, 1974, to Buntin, et al.

The skin contact melt-blown layer 12 has a basis weight from 0.5 oz/yd$^2$ to 2.0 oz/yd$^2$. The preferred basis weight is 1.0 oz/yd$^2$. The melt-blown layer 12 may be formed from any thermoplastic polymer which can be melt-blown, but polypropylene is preferable. Such a melt-blown layer when subjected to heat and moisture will not leach chemicals from the layer onto the skin of the user. The skin contact melt-blown layer 12 may be calendered prior to being incorporated into the fabric laminate 10. Calendering provides bonding between the microfibers within the layer 12 to produce a layer of greater integrity with fewer loose surface fibers. Calendering also produces a layer with less absorbent capacity and a harder surface finish. Consequently, calendering temperature, pressure, and speed may be adjusted in accordance with ordinary experience to provide a skin contact layer 12 which has the desired degree of integrity, absorbent capacity, softness, and absence of loose surface fibers. In general, a bonded melt-blown layer has an absorbent capacity of about 600% by weight while an unbonded melt-blown layer has an absorbent capacity of about 1200%. In connection with the fabric laminate 10, the skin contact layer 12 is impregnated with a skin lotion, cleanser, or other desired facial treatment liquid to at least 30% of the maximum absorbent capacity of the layer 12. Maximum absorbent capacity is measured in accordance with Federal Specification UU-T-595C.

The first barrier layer 14 consists of a thermoplastic film. The thermoplastic film may be formed as a separate sheet of film and then glued to the skin contact layer 12 or alternatively the thermoplastic film 14 may be extruded directly onto the skin contact layer 12 in its semi-tacky state so that it adheres to the skin contact layer 12. Adhesion between the film 14 and the melt-blown layer 12 may be enhanced by heat embossing a decorative pattern onto the two layers. The barrier layer 14 may be formed of any suitable thermoplastic film material, although in general polyethylene is preferred. In one embodiment, the barrier layer 14 is extruded to a nominal thickness of 0.5 mil which produces a barrier film of low porosity with pin hole defects. The pin holes provide an escape for the vapor from the heat retention liquid that builds up during rapid heating of the fabric laminate while still providing sufficient containment of the heat retention liquid vapor during use of the laminate. Porosity of the first barrier layer 14 should be no greater than 50 ft$^3$/min/ft$^2$, and preferably no greater than 20 ft$^3$/min/ft$^2$, as measured in accordance with Federal Test Method 191A, Method 5450 (Frazier Porosity). In another embodiment, the film barrier layer 14 is extruded to a thickness of 1 to 3 mils to assure that the barrier layer 14 has no pin holes and is therefore not porous to either liquid or vapor. When heating is accomplished slowly the vapor can escape through open edge 20, and nonporous barrier 14 can be used to minimize vapor loss during use of the fabric laminate 10. Depending on the heating process used for the fabric laminate 10, the barrier layer 14 may be applied at coating weights from 0.3 to 3 mils in thickness.

The reservoir layer 16 consists of any suitable absorbent which may be used to hold the heat retaining liquid. The absorbent of layer 16 should be capable of holding 400% its weight in liquid and above, preferably 1200% and above. Suitable absorbents include open cell foam, wadding, wood pulp fluff, or co-form. Superabsorbents may be incorporated into the foregoing absorbent media to increase percentage capacity. Co-form is generally preferred and consists of intermingled discrete fibers which are capable of absorbing and holding the heat retention liquid. The production of the co-form layer 16 is in accordance with the disclosure in Anderson et al. U.S. Pat. No. 4,100,324. The co-form layer 16 may include combinations of natural and man-made fibers. The melt-blown fibers of the co-form layer may be made from polypropylene, polyethylene, polyester, or nylon. Generally polypropylene is preferred. The staple length fibers of the co-form layer may be cellulose, cotton, flax, jute, silk, polypropylene, polyethylene, polyester, rayon, or nylon. Because of its cost, cellulose is preferred in connection with the absorbent layer 16 for the staple length fibers. Particularly, the co-form layer is preferably a 70/30 mixture of wood pulp (staple length) to polypropylene (melt-blown) fibers. The weight ratio of wood pulp/polypropylene may range from blends of 30/70 to blends of 90/10.

The absorbent layer 16 is adhesively attached to the barrier layer 14 by water proof adhesive which is applied to less than 100% of the surface area between the barrier layer 14 and the absorbent reservoir layer 16. Likewise, the absorbent reservoir layer 16 is adhesively attached to the second barrier layer 18 by means of waterproof adhesive which again is spread over less than 100% of the contact area between the absorbent layer 16 and the second barrier layer 18.

The second barrier layer 18 is a thermoplastic film which serves to retain the heat retention liquid and vapor within the reservoir layer. By inhibiting the escape of vapor by means of the second barrier layer, the fabric laminate retains heat better because there is less heat lost due to evaporation.

The fabric laminate 10 as previously discussed, may be advantageously employed as a hot facial pack for applying heated moisturizing liquid, cleanser, or other cosmetic liquid or lotion to the face of a user. Likewise, as previously discussed, by heating the moisturizing liquid and the skin of the user and by maintaining that temperature for a period of time, the skin more rapidly absorbs the moisturizing liquid. Consequently, it is desired that the fabric laminate 10, once heated, to a temperature of about 120° F., retain enough heat so that it takes 8 to 10 minutes before the temperature drops to 96° F. while the fabric laminate 10 remains in contact with the skin of the user. Also, it is desired that the lotion to be applied to the skin of the user be contained only in the surface layer 12 so a minimum amount of lotion may be used in connection with the fabric laminate 10 and that the lotion not be diluted or otherwise contaminated by the heat retention liquid held in the adjacent reservoir layer 16.

The barrier layers 14 and 18 retain vapor in the reservoir layer so that heat is not rapidly lost to evaporation of the heat retention liquid during use of the fabric laminate. The first barrier layer 14 also separates the heat retention liquid contained in reservoir layer 16 from the moisturizing lotion held in skin contact layer 12.

The barrier layer 14 is either nonporous or has a low porosity depending on the method used to heat the fabric laminate 10. If the fabric laminate 10 is heated slowly and evenly such as in a radiant oven, the vapor produced within the reservoir layer 16 can slowly escape through the open edge 20 of the fabric laminate 10 thereby relieving the internal vapor pressure on the reservoir layer 16 so that the laminate does not bulge or burst apart. On the other hand, where the fabric laminate 10 is heated in a microwave oven, the speed of the heating and the unevenness of the heating produced by a microwave of the heat retention liquid in the reservoir layer 16 may create hot spots within the reservoir layer 16. Because the vapor pressure of the hot spots cannot be relieved by slow migration of the vapor to the open edge 20, the vapor will produce substantial pressure against the barrier layers 14 and 18 with the possibility of rupturing such layers. Consequently, as previously described, it may be advantageous to produce a barrier layer 14 which has a number of pin holes in it which naturally result from coating layer of less than 1.0 mil in thickness and advantageously at a thickness of 0.5 mil. The pin holes in the barrier layer 14 provide a low porosity barrier 14 which allows the escape of sufficient vapor during the rapid heating process to relieve internal pressure in the reservoir layer 16. Because the pin holes represent such a small percentage of the area of the barrier layer 14 the barrier layer 14 still serves its function of retaining vapor once the fabric laminate 10 has been heated thereby assisting in the retention of heat when the fabric laminate 10 has been applied to the skin of a user.

The present invention is illustrated in connection with the following examples:

EXAMPLE 1

The skin contact layer 12 was formed of melt-blown polypropylene fibers to a basis weight of 0.1 oz/yd$^2$. The resulting layer 12 was then preferably coated by extrusion to a thickness of 0.5 mil of polyethylene film. The 0.5 mil extrusion coating produces a film having a low porosity as a result of the pin hole flaws that naturally result in such a thin extruded coating of polyethylene. For the sample of Example 1, the 0.5 mil film was simulated by 1.0 mil separate film adhesively attached to the melt-blown layer and punctured manually with a pin.

A co-form layer 16 was formed of wood pulp and polypropylene fibers in a ratio by weight of 70% wood pulp (staple) to 30% polypropylene (melt-blown). The co-form layer was formed at a basis weight of 350 grams per square meter (g/m$^2$). A separate 1.0 mil polyethylene film which formed the second barrier layer 18 was adhesively attached to one side of the co-form layer 16. The co-form with the second barrier layer 18 and the skin contact layer 12 with its barrier layer 14 were then adhesively bonded together to form the fabric laminate 10 shown in FIGS. 1 and 2.

EXAMPLE 2

A second sample of the fabric laminate 10 was formed in the same fashion as Example 1 except that the co-form layer had a basis weight of 190 g/m$^2$.

The two samples from Example 1 and Example 2 were cut into sheets 8 inches by 12 inches. The sample of Example 1 was saturated with water to 40% of its maximum capacity, or about 586% by weight of the co-form absorbent. The sample of Example 2 was saturated with water to about 75% by weight of its maximum capacity, or about 1012% by weight of the co-form absorbent. Both samples were heated to a 130° F., put on a lab bench until they reached a uniform temperature of 120° F., and then were applied to the skin on the leg of a user. The heat retention time was measured as the elapsed time for the temperature to drop from 120° F. to 96° F. In addition, a ordinary towel having approximately the same weight as the two samples was used as a control. The results are set out in the table below:

TABLE 1

Skin Temp. - Prior to use 95° F.
- After use 97° F.
Maximum Safe Temp. - 120° F.

| Time | Example 1 350 Co-form | Example 2 190 Co-form | Control Towel |
|---|---|---|---|
| 0 | 120 | 120 | 120 |
| 1 | 105 | 105 | 100 |
| 2 | 101 | 100 | 97 |
| 3 | 99 | 99 | 95 |
| 4 | 98 | 97 | |
| 5 | 98 | 96 | |
| 6 | 97 | | |
| 7 | 97 | | |
| 8 | 97 | | |
| 9 | 96 | | |
| Product Weight With Water Absorbed | 155 g | 138 g | 137 |

The table shows the remarkable improvement in heat retention achieved over the ordinary towel. A comparison of Examples 1 and 2 shows the improvement resulting from additional absorbent in the reservoir layer without the addition of a proportional amount of water.

Figure 3:
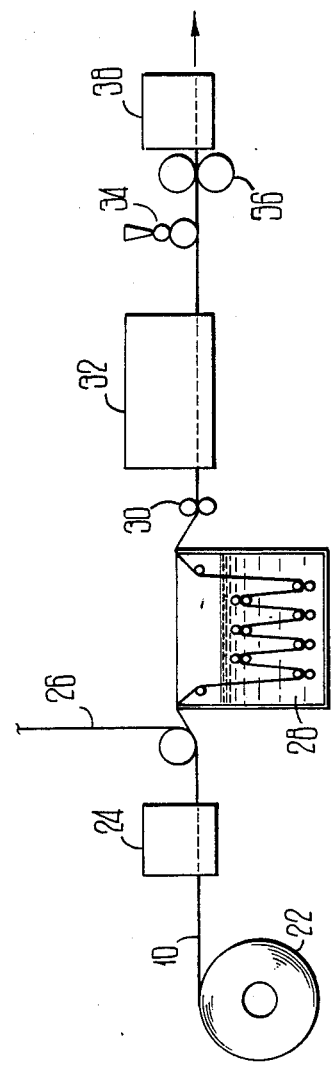
FIG. 3 is a schematic view showing the method for impregnating the fabric laminate of the present invention with the heat retention liquid and the treatment lotion in the reservoir and skin contact layers respectively.

Turning to FIG. 3, there is shown a process for impregnating a fabric laminate 10 with the heat retention liquid and the treatment liquid. The fabric laminate 10 is supplied to the process on a roll 22. The fabric laminate 10 passes through a first die cutter 24 which trims the edges of the web to produce a series of connected oval shapes shown in FIG. 1. The edge waste 26 is removed, and the web of connected ovals is fed into a bath 28 of heat retention liquid. The web passes between a number of rolls in the bath 28 which serve to alternatively squeeze and release the web so that the air is forced out of the reservoir layer 16 through open edge 20, and the heat retention liquid is absorbed into the reservoir layer 16 through open edge 20. After exiting the bath 28, the web 10 passes through rolls 30 which squeeze the fabric laminate 10 so that the desired amount of heat retention liquid remains in the reservoir layer 16. As previously noted, the amount of heat retention liquid remaining in the reservoir layer 16 should be between 25% and 90% of the maximum capacity by weight of the reservoir layer 16. The web is then fed to dryer 32 which dries the skin contact layer 12 to eliminate most of the heat retention liquid which was picked up by the layer 12 in the bath 28. The dryer 32 does not produce sufficient heat to substantially dry out the reservoir layer 16. After exiting the dryer 32, the web passes under doctor rolls 34 which apply the moisturizing lotion to the skin contact layer 12. The lotion is compatible with the heat retention liquid and is concentrated so that any heat retention liquid remaining in the skin contact layer 12 after the dryer 32 dilutes the lotion to the desired consistency. By adjusting the degree of drying in dryer 32 and the concentration of the lotion at doctor rolls 34, the desired consistency of the resulting lotion held in skin contact layer 12 can be achieved. After being impregnated with the lotion to a concentration of at least 30% of the maximum absorbent capacity of the skin contact layer 12, the facial packs are cut apart by a rotary cutter 36. The individual hot packs are then packaged in air tight packages at packaging station 38 for shipment to consumers.

We claim:

1. A thermal retaining fabric laminate comprising in sequence:
   a. a skin contact layer impregnated with a treatment liquid, the skin contact layer comprising an absorbent for retaining the treatment liquid;
   b. a first barrier layer adhered to the skin contact layer;
   c. a reservoir layer adhered to the first barrier layer impregnated with a heat retention liquid, the reservoir layer comprising an absorbent for retaining the heat retention liquid; and
   d. a second barrier layer adhered to the reservoir layer.

2. The laminate of claim 1, wherein the skin contact layer is impregnated to at least 30% of its maximum capacity.

3. The laminate of claim 2, wherein the skin contact layer has a basis weight of between 0.5 and 2.0 oz/yd$^2$.

4. The laminate of claim 1, wherein the first barrier layer has low porosity and separates the moisturizing liquid from the heat retention liquid.

5. The laminate of claim 4, wherein the first barrier layer is a thermoplastic film having a thickness between 0.5 mil and 3.0 mil.

6. The laminate of claim 5, wherein the thermoplastic film is less than 1.0 mil in thickness.

7. The laminate of claim 1, wherein the reservoir layer is impregnated with the heat retention liquid to between 25% and 90% by weight of its maximum absorbing capacity.

8. The laminate of claim 7, wherein the absorbent is a blend by weight of staple length and melt-blown fibers in the range of blends between 30%(staple)/70%(melt-blown) and 90%(staple)/10%(melt-blown).

9. The laminate of claim 1, wherein the laminate has an edge which is unsealed to provide an absorbent path for the heat retention liquid.

* * * * *

UNITED STATES PATENT AND TRADEMARK OFFICE
CERTIFICATE OF CORRECTION

PATENT NO. : 4,913,957

DATED : April 3, 1990

INVENTOR(S) : David C. Strack and La-Donna M. Brown

It is certified that error appears in the above-identified patent and that said Letters Patent is hereby corrected as shown below:

Column 1, line 18, please delete the comma, "," after "thereby";
line 22, please delete "of...cleanser" and substitute
therefor-- in the cleanser of makeup on the user's skin--.

Column 1, line 55, please change "heat" to --hot--.

Column 2, line 21, please change " yards square " to --square yard--.;
line 26, please change " thermal plastic" to --thermoplastic--;
line 47, please change " pin holes" to pinholes--;
line 56, please change " WIth" to --With--.

Column 3, lines 29-30, please change "alternative" to --alternatives--.

Column 4, line 34, change "pin hole" to --pinhole--.

Column 4, line 34 & 45 please change "pin holes" (both occurrences) to
--pinholes--.

Column 5, line 12, please change "water proof" to --waterproof--.

Column 6, lines 4 and 6, please change "pin holes"to --pinholes--;
lines 10 and 11, please change "pin holes" to --pinholes--;
line 27, please change "pin hole" to --pinhole--.

Column 7, line 6, after "Time", please insert --(Min.)--

Signed and Sealed this

Nineteenth Day of January, 1993

Attest:

DOUGLAS B. COMER

Attesting Officer

Acting Commissioner of Patents and Trademarks